United States Patent [19]
Marzoni et al.

[11] Patent Number: 4,820,713
[45] Date of Patent: Apr. 11, 1989

[54] KETOALKANOL ESTERS OF DIHYDROLYSERGIC ACID USEFUL AS 5HT RECEPTOR ANTAGONISTS

[75] Inventors: Gifford P. Marzoni; William L. Garbrecht, both of Indianapolis, Ind.

[73] Assignee: Eli Lilly and Company, Indianapolis, Ind.

[21] Appl. No.: 197,732

[22] Filed: May 23, 1988

Related U.S. Application Data

[62] Division of Ser. No. 782,342, Oct. 1, 1985, Pat. No. 4,772,709.

[51] Int. Cl.$^4$ ............... A61K 31/48; C07D 457/04
[52] U.S. Cl. ............................... 514/288; 546/69
[58] Field of Search ........................ 546/69; 514/288

[56] References Cited

U.S. PATENT DOCUMENTS

| | | | |
|---|---|---|---|
| 3,113,133 | 12/1963 | Hofmann et al. | 546/69 |
| 3,183,234 | 5/1965 | Garbrecht and Lin | 546/68 |
| 3,228,941 | 1/1966 | Bernardi et al. | 546/69 |
| 3,249,617 | 5/1966 | Hofmann et al. | 546/69 |
| 3,580,916 | 5/1971 | Garbrecht | 546/69 |
| 4,230,859 | 10/1980 | Rucman | 546/69 |

FOREIGN PATENT DOCUMENTS 122044 10/1984 European Pat. Off.

OTHER PUBLICATIONS

Cohen et al., *J.P.E.T.*, 227, 327 (1983) (Cohen I).
Cohen et al., *ibid*, 232, 770 (1984) (Cohen II).
Lemberger et al., *Life Sci.*, 35, 71 (1984).
Cohen et al., *Drug Dev. Res.*, 5, 313 (1985) (Cohen IV).
Hingten et al., Abstract 37.4, *Soc. for Neurosci.* (13th Annual Meeting, Nov., 1983).

*Primary Examiner*—Donald G. Daus
*Assistant Examiner*—Cecilia Shen
*Attorney, Agent, or Firm*—Robert A. Conrad; Leroy Whitaker

[57] ABSTRACT

Ketoalkyl esters of 1-substituted-6-$C_{1-4}$ straight chain alkyl (or allyl)ergoline-8$\beta$-carboxylic acid, useful as 5HT receptor antagonists.

20 Claims, No Drawings

KETOALKANOL ESTERS OF DIHYDROLYSERGIC ACID USEFUL AS 5HT RECEPTOR ANTAGONISTS

This application is a division of application Ser. No. 782,342, filed Oct. 1, 1985, now U.S. Pat. No. 4,772,709.

BACKGROUND OF THE INVENTION

Garbrecht, U.S. Pat. No. 3,580,916, discloses a group of lysergic (I) and 9,10-dihydrolysergic acid (II) esters formed with various open chain and cyclic diols. The following structures summarize the disclosure in Garbrecht.

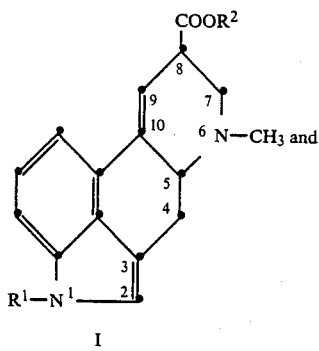

I

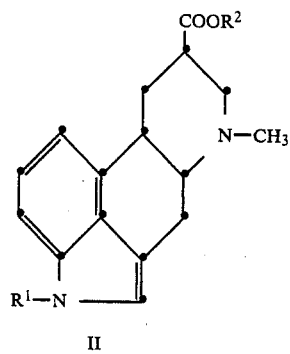

II wherein $R^1$ is H, $C_{1-3}$ alkyl, allyl or benzyl and $R^2$ is $C_2$-$C_8$ monohydroxyalkyl, $C_{2-8}$ dihydroxyalkyl or $C_{5-11}$ monohydroxycycloalkyl having from 5-8 ring carbons. The compounds are useful as serotonin antagonists, the patent stating that "In animals, the compounds act as neurosedatives . . . and are therefore useful in calming . . . animals". The use of compounds according to II, wherein $R^2$ is mono or dihydroxyalkyl, in migraine and other disease states characterized by an excess of peripheral 5HT is disclosed in EPO No. 122,044 published 10-17-84.

The interest in the Garbrecht compounds has thus been intensified by the finding that they had excellent peripheral serotonin antagonist activity against $5HT_2$ receptors and lacked interaction, whether as agonists or antagonists, with other receptors, particularly alpha$_1$ receptors.

The most active peripheral serotonin antagonist from Garbrecht was named 1-isopropyl-6-methyl-8β-(1-methyl-2-hydroxy)propoxycarbonyl-5R-ergoline (II in which $R^1$ is isopropyl and $R^2$ is 1-methyl 2-hydroxypropyl) or 1-methyl-2-hydroxypropyl 1-isopropyl-9,10-dihydrolysergate. In the above name, 5R refers to the beta orientation of the C-5 hydrogen. The C-10 hydrogen is alpha—10R, and the beta orientation at C-8 is R and is the same as in either lysergic or 9,10-dihydrolysergic acid. Both of these acids have a 6-methyl group. An alternate name for the compound is 1-isopropyl-9,10-dihydrolysergic acid 1-methyl-2-hydroxypropyl ester. Cohen et al. J.P.E.T., 227, 327 (1983) (Cohen I) reported that the above compound, given the code number LY53857, was a potent antagonist of vascular contraction to serotonin, which effect is mediated by $5HT_2$ receptors. The compound had minimal affinity for vascular alpha adrenergic, dopaminergic and histaminergic receptors ($K_{dissoc.} \cong 10^{-10}$ vs $\cong 10^{-5}$). Other papers on the pharmacologic properties of LY53857 include Cohen et al., J.P.E.T., 232, 770 (1985) (Cohen III), Harriet Lemberger et al., Life Sciences, 35, 71 (1984), Cohen, Drug Development Res., 5, 313 (1985), (Cohen IV). Cohen and Fuller, EPO No. 122,044 published 10-17-84, referred to above, covers the use of hydroxyalkyl esters of 1-alkyl 9,10-dihydrolysergic acid as peripheral $5HT_2$ receptor antagonists.

Four additional examples of ergolines with a substituent on the indole nitrogen are: U.S. Pat. No. 3,113,133, Hofmann et al., which discloses and claims esters and amides carrying an indole N substituent such as a lower alkyl or alkenyl group or an aralkyl group. The compounds are said to be useful as serotonin antagonists, in treating inflammatory, arthritic and allergic diseases and in treating carcinoid syndrome.

U.S. Pat. No. 3,249,617, Hofmann et al., which covers (indole) N-alkyl or allyl lysergic acids, useful as intermediates.

U.S. Pat. No. 3,228,941, Bernardi et al., which discloses and claims a group of (indole) N-methylergolines—amides, hydroxamides and amidines. The compounds are alleged to have oxytoxic, adrenolytic, hypotensive, sedative and antienteraminic action.

U.S. Pat. No. 4,230,859 to Rucman which discloses dihydrolysergic acid carrying a $C_{1-5}$ alkyl group on the indole nitrogen, useful as intermediates.

Finally, ergolines actually used in the treatment of migraine include the amides: ergotamine, methysergide and ergonovine.

None of the above references indicate that a ketoalkanol ester of an N-alkylated dihydrolysergic acid would have peripheral serotonin antagonist properties.

SUMMARY OF THE INVENTION

This invention provides ergolines of the formula:

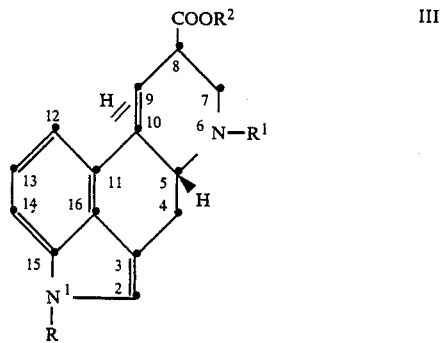

III wherein R is primary or secondary $C_{1-8}$ alkyl, $C_{2-4}$ alkenyl-$CH_2$, $C_{3-8}$ cycloalkyl or $C_{3-6}$ cycloalkyl-substituted $C_{1-5}$ primary or secondary alkyl, the total number of carbon atoms in R not to exceed 8; $R^1$ is H, allyl or $C_{1-4}$ straight-chain alkyl; i.e., methyl, ethyl, n-butyl, or n-propyl, and $R^2$ is

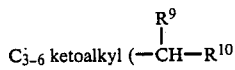

wherein $R^9$ is H, methyl or ethyl and $R^{10}$ is $C_{2-5}$ alkyl containing a keto function) attached to the acidic function through a primary or secondary carbon and pharmaceutically acceptable acid addition salts thereof. Compounds according to III, wherein $R^1$ is other than H, are central or peripheral serotonin $5HT_2$ receptor antagonists lacking interaction at 5HT blocking doses with other receptors. Compounds wherein $R^1$ is H are primarily intermediates.

Groups which R represents include methyl, ethyl, allyl, n-propyl, isopropyl, crotyl, methallyl, n-hexyl, sec-amyl, sec-octyl, n-heptyl, 2,4-dimethylpentyl, 2-ethylpentyl, cyclopropyl, cyclopropylmethyl, cyclopentyl methyl, 2-cyclobutyl ethyl, cyclohexyl, isobutyl, sec.-butyl, 3-methyl-2-butyl, isoamyl, 2-methylhexyl, 3-methylhexyl, 4-methylhexyl(isohexyl), 2-hexyl, 3-hexyl, n-heptyl, 2-heptyl, 3-heptyl, 4-heptyl, n-octyl, 2-octyl, 3-octyl, 4-octyl, isooctyl, 2-methylheptyl, 3-methyl-2-heptyl, and the like. Illustrative of the groups which $R^2$ represents include 2-oxopropyl, 1-methyl-2-oxopropyl, 1-ethyl-2-oxopropyl, 1-methyl-2-oxobutyl, 1-ethyl-2-oxobutyl, 1-methyl-3-oxobutyl, 1-ethyl-3-oxobutyl and the like.

Compounds according to the above formula are named as ergoline derivatives in which the trans-(−) or 5R,10R configuration of the bridgehead hydrogens is specified (The same configuration as in the naturally-occurring 9,10-dihydro ergot alkaloids). In U.S. Pat. No. 3,580,916, a different naming system is used; the basic ring system is named as a 6aR,10aR-4,6,6a,7,8,9,10,10a-octahydroindolo[4,3-f,g]quinoline. Illustratively, by the alternate naming system 9,10-dihydrolysergic acid becomes 6aR,10aR-7-methyl-4,6,6a,7,8,9,10,10a-octahydroindolo[4,3-f,g]quinoline-9β-carboxylic acid. Another equally valid name for 9,10-dihydrolysergic acid is 6-methyl-8β-carboxyergoline. We prefer to use the trivial name "ergoline" with the numbering system specified in III above when $R^1$ is other than methyl and the 9,10-dihydrolysergic name when $R^1$ is methyl.

Pharmaceutically-acceptable acid addition salts of the compounds of formula III include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methoxybenzoate, phthalate, terephthalate, benzenesulfonate, toluenesulfonate, chlorobenzenesulfonate, xylenesulfonate, phenylacetate, phenylpropionate, phenyl-butyrate, citrate, lactate, β-hydroxybutyrate, glycollate, malate, tartrate, methanesulfonate, propanesulfonate, naphthalene-1-sulfonate, naphthalene-2-sulfonate and the like salts.

Illustrative compounds of this invention include:

1,6-diethyl-8β-(2-keto)propyloxycarbonylergoline succinate 1-methyl-6-ethyl-8β-(1-methyl-2-keto)butyloxycarbonylergoline hydrochloride 1-n-propyl-6-allyl-8β-(1-ethyl-3-keto)butyloxycarbonylergoline sulfate 1-isopropyl-6-n-propyl-8β-(1-methyl-2-keto)propyloxycarbonylergoline hydrobromide 3-oxobutyl 1-methyl-9,10-dihydrolysergate 4-oxopentyl 1-ethyl-9,10-dihydrolysergate 1-methyl-4-oxopentyl 1-allyl-9,10-dihydrolysergate 1-allyl-6-ethyl-8β-(3-keto)butyloxyergoline tartrate and the like.

The preparation of compounds represented by formula III in which $R^1$ is $CH_3$ is set forth in Reaction Scheme 1.

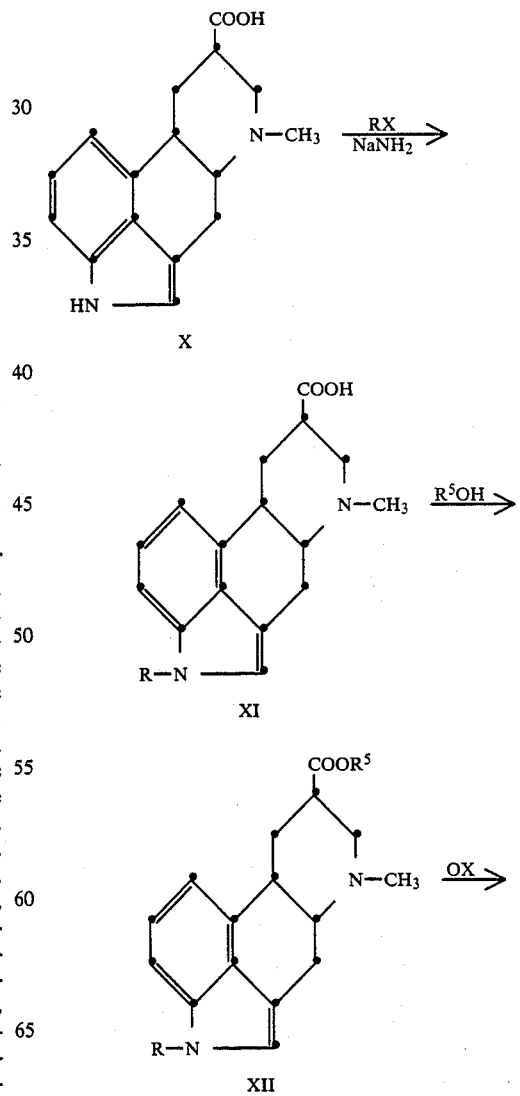

Reaction Scheme 1

-continued

Reaction Scheme 1

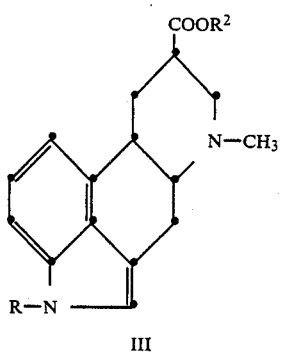

III wherein R and $R^2$ have their previous meaning, $R^5$ is $C_{3-6}$ alkyl containing a secondary hydroxyl group, and $R^5OH$ is a primary or secondary alcohol.

In Reaction Scheme 1, steps 1 and 2 (X→XI→XII) are based on Garbrecht, U.S. Pat. No. 3,580,916. According to the Garbrecht procedure, dihydrolysergic acid is first alkylated on the indole nitrogen using standard procedures—base plus an alkyl halide. Liquid ammonia is a convenient solvent with sodamide as the base and methyl, ethyl, isopropyl or n-propyl iodide or allyl chloride or bromide as the alkylating agent. (See also U.S. Pat. No. 3,183,234-Garbrecht and Lin, which contains general directions and a specific example of the above alkylation procedure).

Alternatively, according to the procedure of Marzoni, Ser. No. 782,339 filed this even date, 9,10-dihydrolysergic acid can be reacted with an aryl sulfonate, $R-O-SO_2$-phenyl-Y where R has its previous meaning and Y is $CH_3$, $NO_2$ or Br in the presence of an alkali metal hydroxide and an aprotic solvent, conveniently KOH in DMSO, to yield the desired N-1 derivative.

With the indole nitrogen substituent in place, the next step in the synthetic procedure is esterification. This procedure requires relatively mild reaction conditions according to U.S. Pat. No. 3,580,916; i.e., preferably at 0°-60° C. The reaction is, however, an otherwise standard acid-catalyzed esterification. The free acid and dihydroxyalkane ($R^5OH$) are the reactants and a convenient work-up of the esterification mixture involves partioning between water and a water-immiscible solvent; $(CH_2Cl)_2$ for example.

Finally, the secondary alcohol group of the ester is oxidized to a ketone, yielding the ketoalkyl esters of this invention where $R^1$ is methyl (esters of 9,10-dihydrolysergic acid). It should be noted that, if the alkandiol ($R^5OH$) is not symmetrical, the resulting ester may be a mixture; i.e., if the diol is 1-ethyl-2-hydroxypropanol, a mixture of the 1-ethyl-2-hydroxypropyl and 1-methyl-2-hydroxybutyl esters. These esters can be separated mechanically, or the mixture can be oxidized and the keto esters separated. However, since differences in pharmacologic activity between any two such isomeric esters would not be expected to be large (less than an order of magnitude), the mixture could be employed as such. However, it will be apparent that use of a symmetrical diol such as butane-2,3-diol would be preferred since its use would avoid the aforesaid isomer problem. However, if the diol contains a primary alcohol, reaction conditions can be employed which favor reaction on the primary alcohol group; for example secondary alcohols react more slowly than primary alcohols in a standard acid-catalysed esterification.

Suitable oxidizing agents for the final step of Reaction Scheme 1 include acetic anhydride/DMSO, dicyclohexylcarbodiimide, chromate salts, positive halogen agents such as $Ca(OCl)_2$, NaOCl and the like.

If the desired final product is not a dihydrolysergic acid ester, but is a 6-ethyl, 6-n-propyl, 6-n-butyl or 6-allyl derivative, the replacement of the 6-methyl group must take place prior to esterification with a alkandiol and oxidation of the ester; i.e., on an $N^1$-alkyl 9,10-dihydrolysergic acid lower alkyl ester. Replacement of the 6-methyl with ethyl, n-propyl, allyl, n-butyl or the like, can be carried out by the procedure of Kornfeld and Bach, U.S. Pat. No. 4,166,182, whereby the N-methyl group is reacted with cyanogenbromide to form an N-cyano derivative. The cyano group is then removed by hydrogenation using zinc dust and hydrochloric acid, or, preferably, by hydrolysis with base in an inert solvent. NaOH in ethylene glycol is a convenient hydrolysis medium. This procedure yields a 1-substituted-$8\beta$-carboxyergoline since the lower alkyl ester group is also hydrolysed. Reesterification with $R^5OH$, as by the previous procedure, yields an hydroxyalkyl 1-substituted ergoline-$8\beta$-carboxylate. This hydroxyalkyl ester is then oxidized to yield the corresponding ketone. The resulting secondary amine ester can then be alkylated or allylated in DMF solution in the presence of a base such as sodium carbonate, to give a product according to formula III in which $R^1$ is other than methyl.

This N-6 alkylation procedure is graphically illustrated in Reaction Scheme 2 below.

Reaction Scheme 2
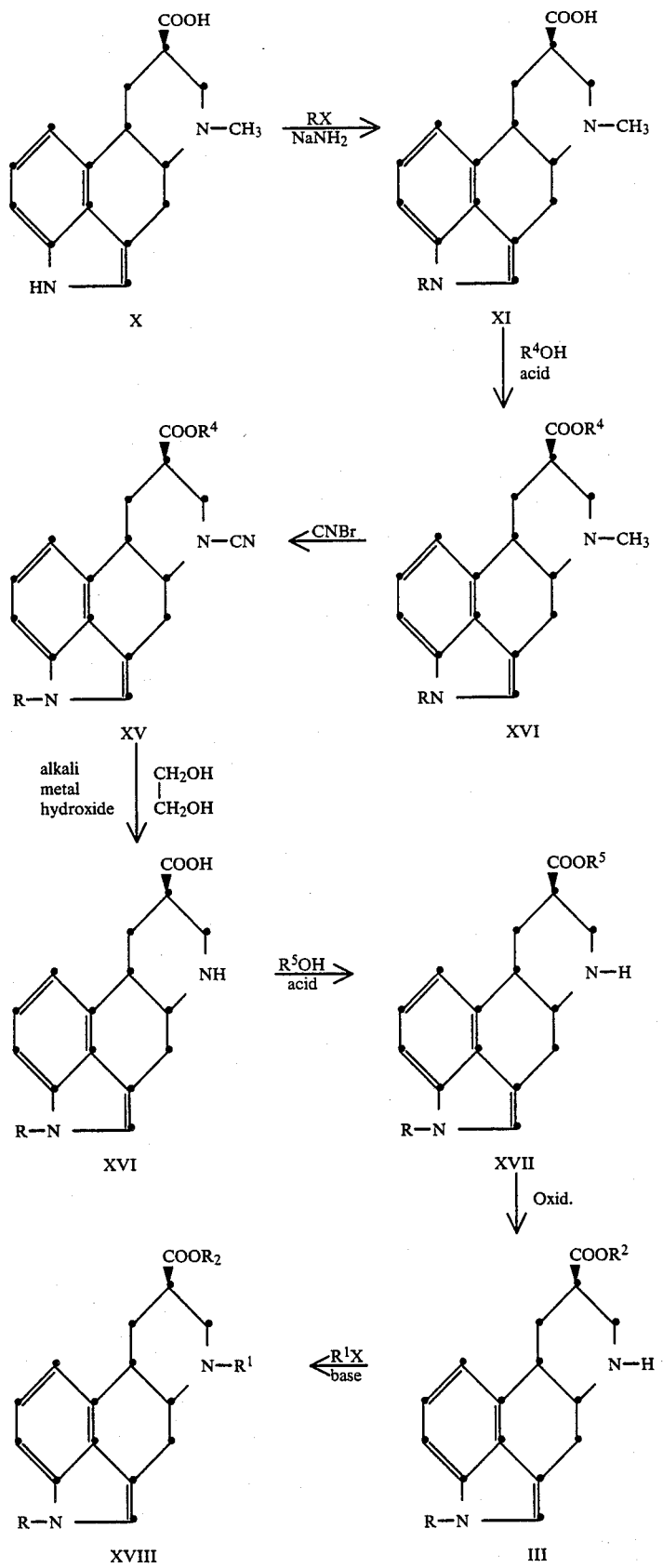

wherein $R^4$ is $C_{1-2}$ alkyl, $R^1$ and R are as previously defined and $R^5$ is hydroxy $C_{3-6}$ alkyl in which the hydroxyl group is secondary.

In the Reaction Scheme 2, 9,10-dihydrolysergic acid (X) is alkylated on the indole nitrogen with an R-hal where "hal" is a halide such as I, Cl or Br using sodamide to create the reactive anion. Alternatively, the procedure of Marzoni, Ser. No. 782,339, filed this even date in which an aryl sulfonate, R-O-SO$_2$-phenyl-Y, is reacted with the indole nitrogen in the presence of an alkali metal halide in an aprotic solvent can be used. The N-1 alkyl or allyl product (XI) is then esterified with a lower alkanol $R^4$OH (a $C_{1-2}$ alkanol preferably) to yield the N-1 alkylated ester (XIV). This compound is then reacted with CNBr by standard procedures to replace the N-6 methyl group and form an N-cyano derivative (XV). Removal of the cyano group under the preferred basic conditions yields a 1-R-9,10-dihydro-6-desmethyllysergic acid (XVI), since the basic conditions also saponifies the C-8 ester group. Next, the 1-R-6-desmethyldihydrolysergic acid (or 1-R-8β-carboxyergoline) is re-esterified with a desired alkanediol ($R^5$OH) to yield the N-6-desmethyl ester (XVII). The secondary hydroxyl in the side chain is now oxidized to a ketone group to yield an ergoline ketoalkyl ester (XVIII). The piperidine ring nitrogen (N-6) is then realkylated with a $C_{1-4}$ alkyl or allyl halide and base under standard conditions to yield the compounds of this invention (III).

It might seem redundant to realkylate at N-6 with methyl since that group is present in the 9,10-dihydrolysergic acid starting material. However, the process would enable one to insert a "tagged" ($C^{14}$ or $H^3$) methyl group for metabolic studies.

The above procedure for replacing the N-methyl of 9,10-dihydrolysergic acid is specifically exemplified in the copending application of Whitten, Garbrecht, Marzoni and Parli, Ser. No. 782,337 filed this even date.

The above procedures are particularly useful where the esterifying alcohol $R^5$OH is symmetrical. Alternate procedures are available for the preparation of ketoalkyl esters of 1-alkyl or allyl-9,10-dihydrolysergic acid and related N-6 homologues whereby a keto alcohol is used directly to yield a compound according to III. Alternatively, a "blocked" $C_{3-6}$ keto alcohol can be used to form the ester; i.e., a ketal of 2-keto propanol can be formed with ethylene glycol. The primary hydroxyl is then replaced by chloro (using SOCl$_2$) and the ketal chloride reacted with the sodium salt of the 1-R-9,10-dihydrolysergic acid. The ketal protecting group is removed by treatment with acid. Obviously, the usual acid catalyzed esterification could not be used with an ketalalkanol because the ketal group would come off during such esterification and alternate procedures available in the art should be used. Also, if it is desirable to avoid an acid catalyzed reaction with a ketoalkanol, a carboxy activating group can be employed to form the ester under non-acidic conditions; i.e., acid chloride or bromide with base. Also carboxy activating agents such as carbodiimide and azolide N,N'-carbonylimidazole can be employed.

Alternatively, a keto alcohol in which the ketone group is protected, as by ketal formation, can be employed in the esterification procedure in Reaction Scheme 2, to yield an ergoline ester lacking an N-6 substituent, analogous to XVII. Alkylation of allylation at N-6 then yields a further intermediate containing an ester with a protected keto group, XIX

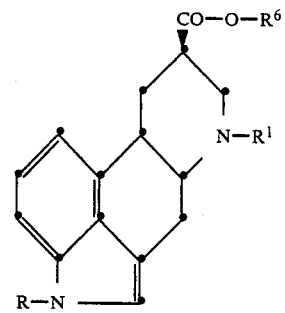

wherein $R^6$ is a $C_{3-6}$ protected

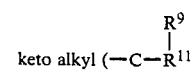

wherein $R^9$ has its previous meaning and $R^{11}$ is $C_{2-5}$ alkyl containing a protected keto function; for example —CH$_2$—C(OC$_{1-2}$ alk)$_2$—CH$_3$ or

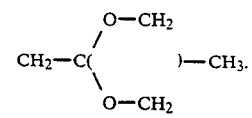

Treatment of XIX with acid then removes the protecting group to yield a ketoalkyl ester of a 1-substituted-9,10-dihydrolysergic acid or a 1-substituted-6-alkyl (or allyl) ergoline-8β-carboxylic acid.

The $C_{3-6}$ alkanediols ($R^5$OH) used to esterify the 1-substituted-9,10-dihydrolysergic acid (or N-6 homologues or congeners thereof) as the last intermediate prior to oxidation of the secondary alcohol to a ketone, will have at least one center of assymmetry, the carbon carrying the secondary alcohol. The diol will also have a second assymetric carbon if the other hydroxyl is secondary. Where the esterifying hydroxyl is primary, the final keto alkyl ester will not have an assymetric center since the assymmetric center in the starting alcohol will be removed by the oxidative process. If the esterifying hydroxyl is secondary, however, the final product will have four assymetric carbons C-6, C-8, C-10 and the side chain assymmetric carbon attached to the carboxyl oxygen. The 9,10-dihydrolysergic acid or ergoline-8β-carboxylic acid assymetric carbons are all R and the side chain carbon in the ketoalkyl group can be S or R. The parent alcohol will then have four stereoisomers, RR, RS, SR and SS. Where the diol is symmetrical, as in butane-2,3-diol, a plane of symmetry exists and there are only three stereoisomers, RR, SS and RS (same as SR). However, esterification removes the plane of symmetry and there are two more diastereoisomers (as with a non-symmetrical diol) designated as RRR-RR, RRR-SR, RRR-RS, and RRR-SS yielding only two keto esters after oxidation (RRR-S and RRR-R).

This invention is further illustrated by the following specific example.

EXAMPLE 1

Preparation of R-1-Methyl-2-oxopropyl-1-isopropyl-9,10-dihydrolysergate

Two-thirds of a gram of R,R-1-methyl-2-hydroxypropyl-1-isopropyl-9,10-dihydrolysergate maleate was partitioned between 50 ml of ethylene dichloride and 50 ml of saturated aqueous sodium bicarbonate. The organic layer, shown by TLC (chloroform/methanol/acetic acid, 18:6:1) to be one-spot material, was dried and the solvent evaporated in vacuo. The crystalline residue (0.38 g) was mixed with 1 ml DMSO (dimethylsulfoxide) and 7 ml of acetic anhydride. The reaction mixture was stirred overnight at room temperature. HPLC indicated absence of starting material. 10 ml of ethanol were added and the mixture stirred for one additional hour. The oxidation mixture was partitioned between 75 ml of ethylene dichloride and 75 ml of saturated aqueous sodium bicarbonate. The ethylene dichloride layer was separated and dried. The residue was purified using preparative HPLC over C-18 reverse phase silica; (acetonitrile/water/triethylamine 65:35:0.02;) 100 ml/min; 200 ml fractions. Fractions 9–20, containing R-1-methyl-2-oxopropyl 1-isopropyl-9,10-dihydrolysergate formed in the above oxidation, were combined, partially evaporated and extracted twice with 200 ml portions of ethylene dichloride, and dried. Evaporation of the solvent from the combined extracts gave 0.38 g of ester. The ester was converted to the corresponding maleate salt by dissolving 0.38 g of the free base in 10 ml of ethyl acetate. 0.13 g of maleic acid were added to the solution. A crystalline salt started to precipitate. 100 ml of ether were added and the crystallization mixture chilled (about 0° C.) overnight. Crystals were separated by filtration, and the filter cake washed with ether and dried. Recrystallization from ethyl acetate gave 150 mg of R-1-methyl-2-oxopropyl 1-isopropyl-9,10-dihydrolysergate maleate.

Analysis: Calc.: C, 65.04; H, 6.87; N, 5.62
Found: C, 64.83; H, 7.10; N, 5.43.

The above procedure was carried out on S,S-1-methyl-2-hydroxypropyl 1-isopropyl-9,10-dihydrolysergate. 0.54 g of the maleate salt of this alcohol were converted to the free base and the free base oxidized with acetic anhydride-DMSO reagent to yield 0.36 g of S-1-methyl-2-oxopropyl 1-isopropyl-9,10-dihydrolysergate which free base was converted to the maleate salt by the procedure of the above example; yield of maleate salt = 170 mg; mass spectrum - molecular ion (of free base) at 382.

Analysis: Calc.: C, 65.04; H, 6.87; N, 5.62;
Found: C, 64.80; H, 7.11; N, 5.32.

HPLC indicated the product contained 88.1% of the S isomer and 6.7% of the R isomer.

Starting materials useful in preparing the compound of this invention, as set forth in the above examples, are synthesized as follows.

Preparation I 2R,3R 1-Methyl-2-hydroxypropyl 1-isopropyl-9,10-dihydrolysergate A reaction mixture, prepared from 4 g of 1-isopropyl-9,10-dihydrolysergic acid, 4.05 g of p-toluenesulfonic acid monohydrate and 40 g of 2R,3R-(−)-butandiol (commercially available) was heated to about 60° C. for about 18 hours. At this time, all solids had dissolved and TLC (CHCl$_3$/MeOH/acetic acid 9:3:0.5) showed absence of starting material. The reaction mixture was cooled and was then added to 160 ml of purified water. The pH of the solution was adjusted to about 8.0 with 28% aqueous ammonium hydroxide. The alkaline mixture was stirred and then filtered. The filter cake was rinsed with water. The filter cake, containing 2R,3R 1-methyl-2-hydroxypropyl 1-isopropyl-9,10-dihydrolysergate formed in the above reaction, weighed 3.96 g (80.5% crude yield); MP = 193°–200° C.; molecular ion at 384.

Analysis: Calc.: C, 71.84; H, 8.39; N, 7.29;
Found: C, 71.58; H, 8.50; N, 7.02.

The maleate salt was prepared in 92 ml methanol using a slight molar excess of maleic acid. Ether (540 ml) was added to the cooled solution to the point of incipient precipitation. Crystals of the maleate salt which precipitated were collected by filtration. The filter cake was dried; weight = 3.54 g; MP = 182°–183.5° C.;

$[\alpha]_d^{25} = -58.5°$

Analysis: Calc.: C, 64.78; H, 7.25; N, 5.60;
Found: C, 64.68; H, 7.33; N, 5.76.

An additional 1.03 g of maleate salt were recovered from the filtrate.

Preparation II

Preparation of 2S,3S 1-Methyl-2-hydroxypropyl 1-isopropyl-9,10-dihydrolysergate

A reaction mixture was prepared from 1.00 g of 1-isopropyl-9,10-dihydrolysergic acid, 1.0 g of p-toluenesulfonic acid, 0.5 g of 2S,3S-O-isopropylidene L-butanediol [prepared by the method of Platner and Rapaport *J.A.C.S.*, 93 1756 (1971)], 0.16 g of water and 15 ml of acetonitrile. The reaction mixture was heated to reflux temperature for about 48 hours. The reaction mixture was cooled and the solids which precipitated were separated by filtration. The filter cake was discarded. The filtrate was evaporated to dryness and the residue partitioned between 50 ml of (CH$_2$Cl)$_2$ and 50 ml of water. The pH of the aqueous layer was adjusted to about 9.0 with 28% aqueous ammonium hydroxide. The two layers were thoroughly mixed. The layers were separated. The organic layer was emulsified and was therefore washed with 50 ml of brine. The organic layer was dried and the solvent evaporated therefrom. The residue (0.9 g) was purified by HPLC over a C-18 column(eluate = CH$_3$CN/H$_2$O 65:35 plus a trace of Et$_3$N).

2S,3S 1-methyl-2-hydroxypropyl 1-isopropyl-9,10-dihydrolysergate thus purified was converted to the maleate salt as in the previous preparation. 1.3 g of base plus 0.43 g of maleic acid gave 1.2 g of salt; MP = 194°–195.5° C. (with decomposition); molecular ion of base = 384;

$[\alpha]_d^{25} = -43.37°$

Analysis: Calc.: C, 64.78; H, 7.25; N, 5.60;
Found: C, 64.67; H, 7.16; N, 5.42.

This invention also provides novel methods whereby 5HT$_2$ receptors are blocked. Such methods are potentially useful in treating disease states in which an excess of circulating serotonin is a major contributing cause. These disease states include hypertension, anorexia nervosa, depression, mania, carcinoid syndrome, migraine and vasospasm. The compounds according to III above show relatively slight affinity for other receptors, $\alpha_1$, $\alpha_2$, $\beta$, histamine, carbachol etc. and thus are highly selective in their action. Formulations in which a compound of this invention is an active ingredient also form another aspect of this invention.

In order to demonstrate that compounds according to formula III have an extremely high affinity for 5HT$_2$ receptors, apparent dissociation constants ($K_b$) as a measure of affinity for 5HT$_2$ receptors, expressed as the negative logarithm, have been determined according to the following protocol.

Male Wistar rats (150-300 gram weight) were killed and their external jugular veins and thoracic aortas dissected free of connective tissue, cannulated in situ and placed in a modified Krebs' bicarbonate buffer in a suitable tissue bath. Two L-shaped 30-gauge stainless-steel hypodermic needles were inserted in each cannula and the dissected vessels gently pushed onto the needles. One needle was attached with thread to a stationary glass rod and the other to the transducer. [The procedure employed was that described by Hooker, Calkins and Fleisch, *Blood Vessels,* 14, 1, (1977) for use with circular smooth muscle preparations.]

The modified Krebs' bicarbonate buffer had the following makeup: (concentrations in millimoles): sodium chloride, 118.2; potassium chloride, 4.6; calcium chloride dihydrate, 1.6; potassium dihydrogenphosphate, 1.2; magnesium sulfate, 1.2; dextrose, 10.0; sodium bicarbonate, 24.8; and water q.s. to 1000 g. The tissue baths were maintained at 37° C. and were aerated with 95% oxygen-5% CO$_2$. An initial optimum resting force of 1 and 4 g was applied to the jugular vein and aorta, respectively. Isometric contractions were recorded as changes in grams of force on a Beckman Dynograph with Statham UC-3 transducers and microscale accessory attachment. Tissues were allowed to equilibrate 1 to 2 hours before exposure to drugs. Control responses to serotonin in the jugular vein and to norepinephrine in the aorta were obtained. The vessels were then incubated with appropriate concentrations of antagonist for one hour. Responses to serotonin or to norepinephrine were then repeated in the presence of the antagonist. Contraction to serotonin was evaluated in the jugular vein since this tissue produces marked responses to serotonin in the absence of alpha receptors—see Cohen and Wiley, *J. Pharm. Exp. Ther.,* 205, 400 (1978). Alpha receptor antagonist activity was evaluated in the aorta.

Apparent antagonist dissociation constants were determined for each concentration of antagonist according to the following equation:

$$K_B = \frac{[B]}{[\text{dose ratio} - 1]}$$

wherein [B] is the concentration of the antagonist and the dose ratio is the ED$_{50}$ of the agonist in the presence of the antagonist divided by the control ED$_{50}$. These results are then expressed as the negative logarithm of $K_B$. The $-\log K_B$ values obtained for compounds of this invention are given below in Table 1.

Apparent Dissociation Constants for 5HT$_2$ receptors determined in the rat jugular vein.

In mammals, hypertension may be mediated through 5HT$_2$ receptors. Thus, compounds of formula III would be expected to lower blood pressure in humans as does ketanserin, another 5HT$_2$ blocker, but without the side effects attributable to the alpha adrenergic receptor blockade of ketanserin.

In carrying out our novel therapeutic process, a pharmaceutically-acceptable salt of a drug according to formula III above formed with a non-toxic acid is administered orally or parenterally to a mammal with an excess of circulatory serotonin in which mammal is desirable to block 5HT$_2$ receptors in order to alleviate symptoms attributable to excessive serotonin levels such as high blood pressure and migraine. For parenteral administration, a water soluble salt of the drug is dissolved in an isotonic salt solution and administered by the i.v. route. For oral administration, a pharmaceutically-acceptable salt of the drug is mixed with standard pharmaceutical excipients such as starch and loaded into capsules or made into tablets, each containing 0.1 to 100 mg of active drug. Dosage levels of from 0.1-10 mg/kg have been found to be effective in blocking 5HT$_2$ receptors. Thus, the oral dosage would be administered 2-4 times per day, giving a daily dosage range of about 0.003 to about 10.0 mg./kg. per day.

Other oral dosage forms, suspensions, elixirs and tablets, can also be utilized and are preparable by standard procedures.

We claim:

1. A compound of the formula:

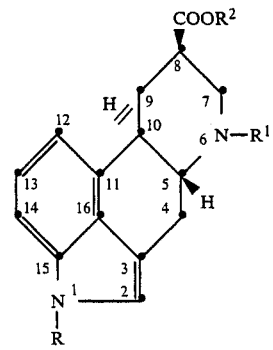

wherein R is primary or secondary C$_{1-8}$ alkyl, CH$_2$—C$_{2-4}$ alkenyl, C$_{3-8}$ cycloalkyl or C$_{3-6}$ cycloalkyl-substituted $C_{1-5}$ primary or secondary alkyl, the total number of carbon atoms in R not to exceed 8; $R^1$ is H, allyl or $C_{1-4}$ straight chain alkyl, and $R^2$ is $C_{3-6}$ ketoalkyl and pharmaceutically-acceptable salts thereof.

2. A compound according to claim 1 in which R is isopropyl.

3. A compound according to claim 1 in which $R^1$ is H.

4. A compound according to claim 1 in which $R^1$ is $C_{1-4}$ straight chain alkyl.

5. A compound according to claim 1 in which $R^2$ is wherein is H, methyl or ethyl and $R^{10}$ is $C_{2-5}$ alkyl containing a ketone function.

6. A compound according to claim 5 in which $R^2$ is S-1-methyl-2-oxopropyl.

7. A compound according to claim 5 in which $R^2$ is R-methyl-2-oxopropyl.

8. A compound according to claim 1, said compound being S-1-methyl-2-oxopropyl 1-isopropyl-9,10-dihydrolysergate.

9. A compound according to claim 1, said compound being R-1-methyl-2-oxoproyl 1-isopropyl-9,10-dihydrolysergate.

10. A method of blocking $5HT_2$ receptors which comprises administering to a mammal having an excess of serotonin centrally or peripherally an $5HT_2$ blocking dose of a compound according to claim 1.

11. A method of treating hypertension which comprises administering to a hypertensive mammal, a hypotensive dose of a compound according to claim 4.

12. A method of treating migraine which comprises administering to a mammal suffering from migraine, a migraine relieving dose of a compound according to claim 4.

13. A method of treating vasospasm which comprises administering to a mammal experiencing vasospasm, a vasospasm relieving dose of a compound according to claim 4.

14. A process according to claim 10 in which R-1-methyl-2-oxopropyl 1-isopropyl-9,10-dihydrolysergate is the drug employed.

15. A process according to claim 10 in which R-1-methyl-2-oxopropyl 1-isopropyl-9,10-dihydrolysergate is the drug employed.

16. A process according to claim 11 in which S-1-methyl-2-oxopropyl 1-isopropyl-9,10-dihydrolysergate is the drug employed.

17. A process according to claim 11 in which S-1-methyl-2-oxopropyl 1-isopropyl-9,10-dihydrolysergate is the drug employed.

18. A compound of the formula

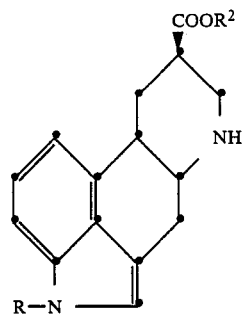

wherein R is primary or secondary $C_{1-8}$ alkyl, $CH_2$—$C_{2-4}$ alkenyl, $C_{3-8}$ cycloalkyl or $C_{3-6}$ cycloalkyl-substituted $C_{1-5}$ primary or secondary alkyl, the total number of carbon atoms in R not to exceed 8; and $R^2$ is $C_{3-6}$ ketoalkyl.

19. An intermediate of the structure

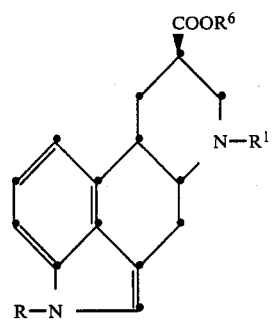

wherein R is primary or secondary $C_{1-8}$ alkyl, $CH_2$—$C_{2-4}$ alkenyl, $C_{3-8}$ cycloalkyl or $C_{3-6}$ cycloalkyl-substituted $C_{1-5}$ primary or secondary alkyl, the total number of carbon atoms in R not to exceed 8; $R^1$ is H, $C_{1-4}$ straight chain alkyl or allyl; and $R^6$ is a primary or secondary $C_{3-6}$ alkyl containing a protected keto group.

20. A compound according to claim 19 in which $R^6$ is —$CHR^9R^{11}$ wherein $R^9$ is H, methyl or ethyl and $R^{11}$ is $C_{2-5}$ alkyl containing a $C(OC_{1-2}\ alkyl)_2$ group or a

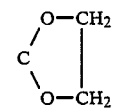

group.

* * * * *

UNITED STATES PATENT AND TRADEMARK OFFICE
CERTIFICATE OF CORRECTION

PATENT NO. : 4,820,713
DATED : April 11, 1989          Page 1 of 2
INVENTOR(S) : Gifford P. Marzoni et al.

It is certified that error appears in the above—identified patent and that said Letters Patent is hereby corrected as shown below:

In Column 14, lines 5-22, please add the following table:

Table 1

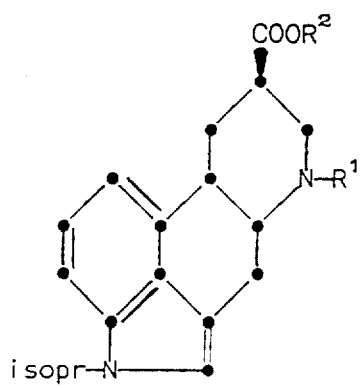

| Compound | | | $5HT_2$ |
|---|---|---|---|
| $R^1$ | $R^2$ | salt | $-Log\ K_b \pm S.E.$ |
| $CH_3$ | $R-CH(CH_3)COCH_3$ | maleate | $9.45 \pm .05$ |
| $CH_3$ | $S-CH(CH_3)COCH_3$ | maleate | $9.57 \pm .10$ |

UNITED STATES PATENT AND TRADEMARK OFFICE
CERTIFICATE OF CORRECTION

PATENT NO. : 4,820,713

DATED : April 11, 1989

INVENTOR(S) : Gifford P. Marzoni et al.

It is certified that error appears in the above—identified patent and that said Letters Patent is hereby corrected as shown below:

Column 15, lines 11 and 12, Claim 5, "$R^2$ is wherein is H," should read --$R^2$ is -$CHR^{10}R^9$ wherein $R^9$ is H,--

Column 15, line 23, Claim 9, "-2-oxoproyl" should read -- -2-oxopropyl --.

Column 15, line 28, Claim 10, "claim 1" should read --claim 4--.

Signed and Sealed this

Fifteenth Day of May, 1990

Attest:

HARRY F. MANBECK, JR.

Attesting Officer

Commissioner of Patents and Trademarks